United States Patent [19]

Claude et al.

[11] Patent Number: 5,562,621

[45] Date of Patent: Oct. 8, 1996

[54] COMMUNICATION SYSTEM FOR LINKING A MEDICAL DEVICE WITH A REMOTE CONSOLE

[75] Inventors: John P. Claude, San Carlos; Frank W. Ingle, Palo Alto; Paul A. Hing, Redwood City, all of Calif.

[73] Assignee: Advanced Cardiovascular Systems, Inc., Santa Clara, Calif.

[21] Appl. No.: 156,568

[22] Filed: Nov. 22, 1993

[51] Int. Cl.⁶ ................................................. A61M 29/00
[52] U.S. Cl. ............................................................ 604/100
[58] Field of Search .................. 128/DIG. 13; 604/100, 604/96, 97, 98, 99, 100–106, 192, 193, 194

[56] References Cited

U.S. PATENT DOCUMENTS

| | | |
|---|---|---|
| 3,488,586 | 1/1970 | Watrous et al. . |
| 3,623,474 | 11/1971 | Heilman . |
| 3,698,381 | 10/1972 | Federico et al. . |
| 3,701,345 | 10/1972 | Heilman et al. . |
| 3,720,199 | 3/1973 | Rishton et al. . |
| 3,985,123 | 10/1976 | Herzlinger et al. . |
| 4,006,736 | 2/1977 | Kranys et al. . |
| 4,056,043 | 11/1977 | Sriramamurty et al. . |
| 4,091,272 | 5/1978 | Richter et al. . |
| 4,106,002 | 8/1978 | Hogue, Jr. . |
| 4,321,014 | 3/1982 | Eburn, Jr. et al. . |
| 4,332,254 | 6/1982 | Lundquist . |
| 4,370,982 | 2/1983 | Reilly . |
| 4,439,185 | 3/1984 | Lundquist . |
| 4,439,186 | 3/1984 | Kuhl . |
| 4,493,704 | 1/1985 | Beard et al. . |
| 4,576,181 | 3/1986 | Wallace et al. . |
| 4,583,917 | 4/1986 | Shah . |
| 4,583,974 | 4/1986 | Kokernak . |
| 4,608,994 | 9/1986 | Ozawa et al. . |
| 4,610,256 | 9/1986 | Wallace . |
| 4,651,738 | 3/1987 | Demer et al. . |
| 4,654,027 | 3/1987 | Dragan et al. . |
| 4,655,749 | 4/1987 | Fischione . |
| 4,677,980 | 7/1987 | Reilly et al. . |
| 4,677,982 | 7/1987 | LLinas et al. . |
| 4,694,409 | 7/1987 | Lehman . |
| 4,723,938 | 2/1988 | Goodin et al. . |
| 4,743,230 | 5/1988 | Nordquest . |
| 4,758,223 | 7/1988 | Rydell . |
| 4,781,192 | 11/1988 | Demer . |
| 4,795,431 | 1/1989 | Walling . |
| 4,796,606 | 1/1989 | Mushika . |
| 4,808,165 | 2/1989 | Carr . |
| 4,832,692 | 5/1989 | Box et al. . |
| 4,838,864 | 6/1989 | Peterson . |
| 4,854,324 | 8/1989 | Hirschman et al. . |
| 4,858,615 | 8/1989 | Meinema . |
| 4,872,483 | 10/1989 | Shah . |
| 4,911,695 | 3/1990 | Lindner . |

(List continued on next page.)

FOREIGN PATENT DOCUMENTS

| | | |
|---|---|---|
| WO90/04987 | 5/1990 | WIPO . |
| WO90/11040 | 10/1990 | WIPO . |
| WO92/06735 | 4/1992 | WIPO . |
| WO92/15359 | 9/1992 | WIPO . |

Primary Examiner—C. Fred Rosenbaum
Assistant Examiner—Manuel Mendez
Attorney, Agent, or Firm—Fulwider Patton Lee & Utecht

[57] ABSTRACT

A communication system using infrared energy to communicate control and data signals from a portable medical device to a remotely located display console. The portable medical device contains a battery for powering the infrared transmission and processing devices and also includes a battery parameter sensor to determine battery status, a temperature sensor, and manufacturing data concerning the portable medical device. Signals from the battery sensor and the temperature sensor are multiplexed with the control and data signals from the portable medical device for IR transmission. The control signals sent from the portable medical device may be used to program various functions of the remote console such as display parameters, console configuration and threshold levels. The display of the remote console presents information through a graphic display.

29 Claims, 8 Drawing Sheets

U.S. PATENT DOCUMENTS

| | | |
|---|---|---|
| 4,919,121 | 4/1990 | Rydell et al. . |
| 4,929,238 | 5/1990 | Baum . |
| 4,940,459 | 7/1990 | Noce . |
| 4,944,726 | 7/1990 | Hilal et al. . |
| 4,952,928 | 8/1990 | Carroll et al. . |
| 4,985,015 | 1/1991 | Obermann et al. . |
| 5,004,472 | 4/1991 | Wallace . |
| 5,007,904 | 4/1991 | Densmore et al. . |
| 5,009,662 | 4/1991 | Wallace et al. . |
| 5,015,233 | 5/1991 | McGough et al. . |
| 5,019,041 | 5/1991 | Robinson et al. . |
| 5,021,046 | 6/1991 | Wallace . |
| 5,047,015 | 9/1991 | Foote et al. . |
| 5,057,078 | 10/1991 | Foote et al. . |
| 5,084,060 | 1/1992 | Freund et al. . |
| 5,135,488 | 8/1992 | Foote et al. . |
| 5,152,776 | 10/1992 | Pinchuk . |
| 5,163,904 | 11/1992 | Lampropoulos et al. . |
| 5,201,753 | 4/1993 | Lampropoulos et al. . |
| 5,215,523 | 6/1993 | Williams et al. . |
| 5,273,537 | 12/1993 | Haskvitz et al. . |
| 5,300,027 | 4/1994 | Foote et al. . |

COMMUNICATION SYSTEM FOR LINKING A MEDICAL DEVICE WITH A REMOTE CONSOLE

BACKGROUND

The invention is generally related to communication systems and more particularly, to a wireless communication link between a medical device and a remotely located console.

Many inflation devices used with dilatation balloon catheters measure the pressure of the inflation fluid and provide a numerical display of the measured pressure at the inflation device itself. However, in addition to a pressure display, it is also desirable for the physician to have certain displays of timer functions. Some physicians use a stopwatch for timing purposes and monitor its time display during the dilatation procedure. This technique can be inconvenient for the physician in that the stopwatch may require both of the physician's hands for its operation and it may have a display which is relatively small and difficult to read. Additionally, the stop watch does not include all pertinent information, such as the number of inflations of this particular balloon and the physician must look elsewhere for that information. Hence it has been recognized by those skilled in the art that it would be desirable to provide a large display having all information, including timing information, desired by the physician during the dilatation procedure.

Where the inflation devices are disposable, the inclusion of extensive electronics in the disposable to provide and display vast amounts of data unacceptably increases the cost of the disposable. One solution is to provide the electronics in a separate console, with a cable connecting the inflation device to the console. A display which includes measured data and timing on a dedicated console may also be made much larger and easier to read. In addition, a dedicated console could provide both numerical and graphical data representations. In many cases, a graphical representation of data proves easier to read from a distance and can present more information in a more readily understandable manner. However, the presence of an electrical cable can sometimes be an inconvenience in that it must traverse the operating area and may interfere with operations, at least in the case where a manual inflation device is used. In the case where the cable must exit the sterile field, sterility is also a concern.

Infrared ("IR") information transmission systems have proven to be of value for short-range transmission of both analog and digital information. The inherent advantages of infrared transmission are apparent; transmission of infrared data does not generate radio frequency interference that might interfere with other instrumentation; and, even more important, the infrared receiver is unaffected by radio frequency interference produced by other devices operating in the vicinity. Known IR systems include music systems where only data is sent from the remote console to the portable device and television systems where only control signals are sent from the portable device to the remote console. In the television system the control signals are used by a processor to control the operation of the system. However, these systems do not incorporate the transmission of both data and control signals from a portable device to a remote console device.

A further consideration is the programming of the remote console. Where the programming must be performed at the console itself, inconvenience to the physician can result. Where the console is located out of the reach of the physician, he or she must move to the console, program the console, and then return to the patient. In addition, the physician's hands may be sterile, making control of the non-sterile console a concern. Where the physician decides to instruct someone else to program the console, that programming performed by the other person may need to be verified by the physician. By having to explain the parameters to be programmed and then confirming that such programming was properly performed, the physician may use more time than if he or she had programmed the console personally. Additionally, some physicians may desire to reset certain numerical or graphical displays after part of a dilatation procedure has been accomplished. Having to move to a remote console to do so may present a major inconvenience. Hence, it would be desirable to allow the physician to reset programming while at the medical device so that the physician doesn't have to change positions or suspend the procedure. However, a concern arises in the case where inadvertent switch activations at the medical device may cause undesired programming changes to occur during the medical procedure. Hence, those skilled in the art have recognized a need for programming control so that certain functions cannot be engaged during the medical procedure.

Although medical IR systems have been proposed, in the experience of the inventors these systems do not also transmit non-patient data, such as the status of the power supply of the portable medical device. Nor do any such systems transmit data regarding the temperature of the inflation fluid used in a dilatation system or combinations of measured data and status of command switches. Hence those concerned with the art have recognized that it would be of value to provide a system which furnishes multiple data items concerning various aspects of the dilatation procedure, operator commands and status of the medical device and which further provides a remote console featuring a relatively large display which permits numerous data items to be read in a graphical format from a distance. The invention satisfies these needs and others.

SUMMARY OF THE INVENTION

Briefly and in general terms, the present invention provides a new and improved communication system for communicating signals between a medical device and a console. The medical device includes a first sensor for sensing a physical or physiological parameter and for providing data signals representative of the sensed parameter to the console. In a more detailed aspect, the medical device further includes at least one control switch for providing control signals to the console. In response to the commands transmitted by the control switch signals, the console employs various modes to process the data signals. The communication system comprises a first circuit disposed at the medical device and coupled to the first sensor and the control switch to process the data signals representing the sensed physical or physiological parameter and the control signals into a predetermined signal pattern. In another detailed aspect, a transmitter disposed at the portable medical device radiates its information in accordance with the predetermined signal pattern. The portable medical device further includes a battery for providing power to the first circuit and the transmitter.

At the console, a receiver receives the predetermined signal pattern and derives the data signals and control signal from that signal pattern. A processor at the console processes the derived data signals and provides graphic display signals in response thereto. A display presents those signals in a graphical format to the user. In a further aspect, a detection circuit may be included to detect the presence of more than one transmitter. If such is detected, an alarm signal may be provided.

In another aspect in accordance with the invention, the transmitter radiates IR energy in accordance with the signal pattern. In one feature, the transmitter includes a plurality of IR light radiating devices oriented at an angle with one another in order to generate the IR radiation in a wide acceptance angle for effective transmission.

In yet a further aspect, the first circuit comprises a multiplexer that receives the data signals from the sensor and the control signal from the control switch and multiplexes them into a multiplexed signal. That multiplexed signal is incorporated into the predetermined signal pattern that is provided to the transmitter to generate the radiated signal.

In another aspect in accordance with the invention, the medical device includes a battery sensor that senses a battery parameter indicative of the remaining life of the battery and provides a signal representative of the battery level. The first circuit is coupled to the battery sensor and receives the battery level signal and processes it into the predetermined signal pattern. In the aspect where a multiplexer is used, the battery level signal is multiplexed with the other signals to generate the predetermined signal pattern. The remote console may both display a battery life indication as well as compare it to a minimum threshold level and provide a warning if the remaining battery life is too low for the portable medical device to continue reliable operation.

In another aspect in accordance with the invention, the portable medical device includes a temperature sensor that senses the temperature of a predetermined portion of the medical device, such as inflation fluid in a dilatation catheter, the temperature sensor providing a temperature signal. The first circuit is coupled to the temperature sensor and receives the temperature signal and processes it into the predetermined signal pattern. Where a multiplexer is included, that temperature signal will also be multiplexed with other signals in forming the predetermined signal pattern.

A memory device is provided in the portable medical device for storing manufacturing data related to specific characteristics of the portable medical device itself. Manufacturing data may include: model number, serial number, date of manufacture, type of sensor; and calibration information such as offset of the sensor, scale factor of the sensor and temperature coefficient of the sensor. Certain of this manufacturing data may be processed by the first circuit to alter the sensor data at the medical device or may be processed into the predetermined signal pattern for transmission by the transmitter to the remote console processor that can then alter the sensor data accordingly.

The system in yet another aspect includes a processor at the remote console that is responsive to control signals from one or more control switches mounted on the portable medical device so that the user of the portable medical device can program the remote console by activation of the control switch at the portable medical device. Through programming, the user can alter the display by selecting the information as well as the format of the information to be displayed. However, in yet another aspect, such programming ability may be disabled if the system has a predetermined status. For example, if a pressure above zero exists.

In a further aspect, the remote console may comprise an historical memory for storing certain data related to procedures in which the system was used. The data in this historical memory may be retrieved and displayed and/or printed as required.

The above and other aspects, features, and advantages of the invention will become apparent from the following more detailed description, when taken in conjunction with the accompanying drawings of an illustrative embodiment.

DETAILED DESCRIPTION OF PREFERRED EMBODIMENTS

Figure 1:
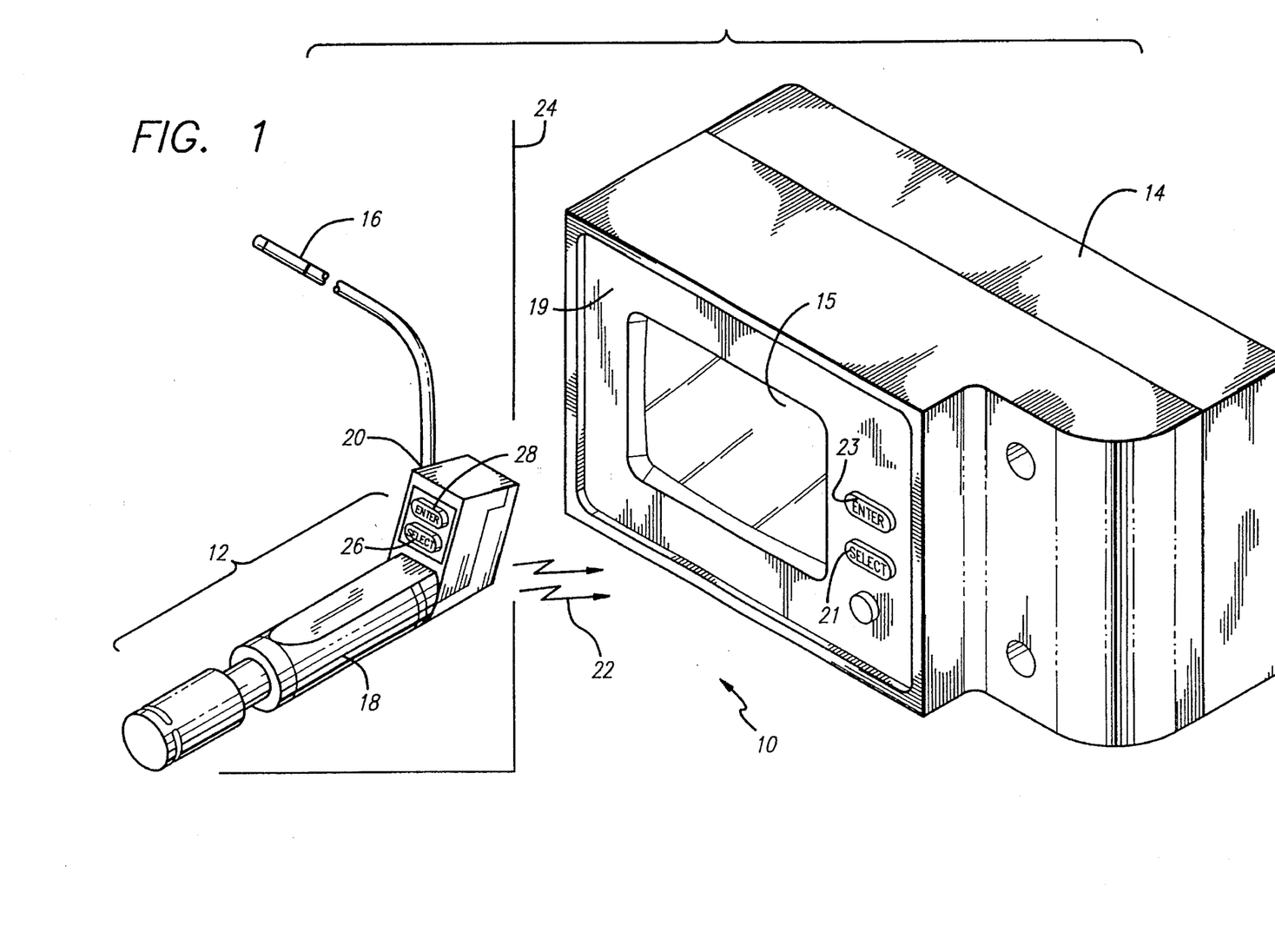
FIG. 1 presents a diagram of a portable medical device having sensors, control switches, and a transmitter coupled by radiated energy to a remote console including a receiver and a display.

Referring now to the figures wherein like reference numerals indicate like or corresponding elements between the different figures, there is shown in FIG. 1 a schematic drawing of a communication system 10 for providing a means of linking a portable medical device 12 with a remote console 14. The portable medical device in this embodiment comprises a dilatation balloon catheter 16 with an inflation/deflation control device 18 connected to its proximal end 20. The inflation/deflation control device 18 provides control over the pressure of the inflation fluid in the balloon and may take forms other than that shown in the figure.

The display console 14 includes a front panel 19 having a screen 15 displaying multiple parameters through a graphical display.

Figure 2:
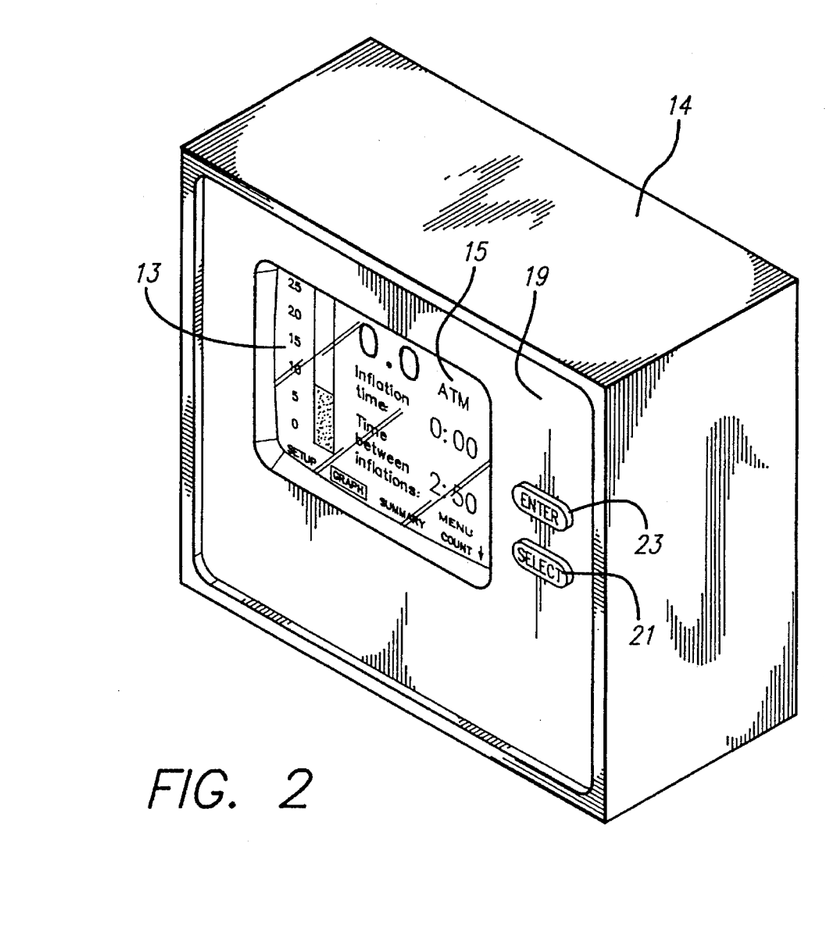
FIG. 2 shows one embodiment of a front panel graphical display.
Figure 3:
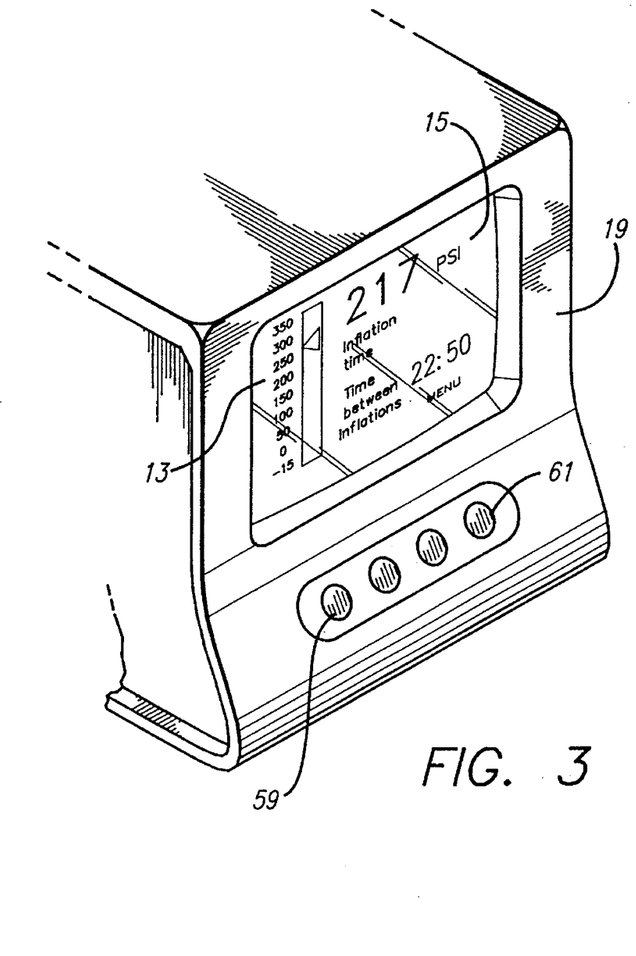
FIG. 3 shows another embodiment of a front panel graphical display having programmable keys.

Referring now to FIGS. 2 and 3, the screens 15 show alphabetical and numerical data along with the graphical vertical bar graph 13. The screens in these embodiments are actually graphical displays, not an alpha-numeric display. In this case, information pertaining to the instant pressure, the elapsed time, and the time between inflations is presented. The vertical bar graph 13 on the screen 15 in this embodiment is a graphical display of the current pressure in the balloon. Other information may be displayed by programming different monitor configurations; FIGS. 2 and 3 present exemplary consoles only.

It has been found that a graphical display in some cases presents information more readily and is more readily understood than an alpha-numeric display that is capable of presenting only numbers and alphabetical characters. In many cases, the alpha-numeric display is capable of presenting such characters in only a single size. As an example, in a high stress situation, a reference to the vertical bar graphs shown in FIGS. 2 and 3 may provide a physician with enough information and quickly enough to enable him or her to make a rapid determination of the status of the medical procedure. By referring to a bar graph, the physician can determine that the pressure presently is almost at the center of the acceptable pressure range or is out of the center area. If more detailed information is desired, the physician can then view the numerical data. In the cases of FIGS. 2 and 3, it will be noticed that the numerical data is also in a format for easier reading. One of the more important of the pressure data is in a larger type than the others.

Although other displays can be used, in the embodiment shown in FIGS. 1, 2, and 3, an electro-luminescent display 52 was used. Specifically, a Finlux MD 320.256 from Lohja Corporation, 20395 Pacifica Drive, #109, Cupertino, Calif. 95014. Additionally, techniques other than a vertical bar chart may be provided. In place of the vertical bar chart and vertically moving arrowhead, different graphical displays of information may be presented. In the case of stored historical data, trend lines (a graph of pressure versus time for example) may be displayed.

Referring now to FIGS. 1 and 2, the front panel includes two switches, labeled "SELECT" 21 and "ENTER" 23. The front panel 19 of FIG. 3 also includes in the embodiment four switches, two of which are indicated by numerals 59 and 61 adjacent the screen 15. As discussed below, these switches may have different functions as programmed.

As indicated by the directional lines 22, the portable medical device 12 is in communication with the remote console 14 through radiation. The right-angle line 24 is meant to indicate that the portable medical device 12 is located in a sterile field while the remote console 14 may be located outside that field.

The portable medical device 12 also includes a pair of switches 26 and 28 that provide control signals when activated, as is discussed in more detail below.

Figure 4:
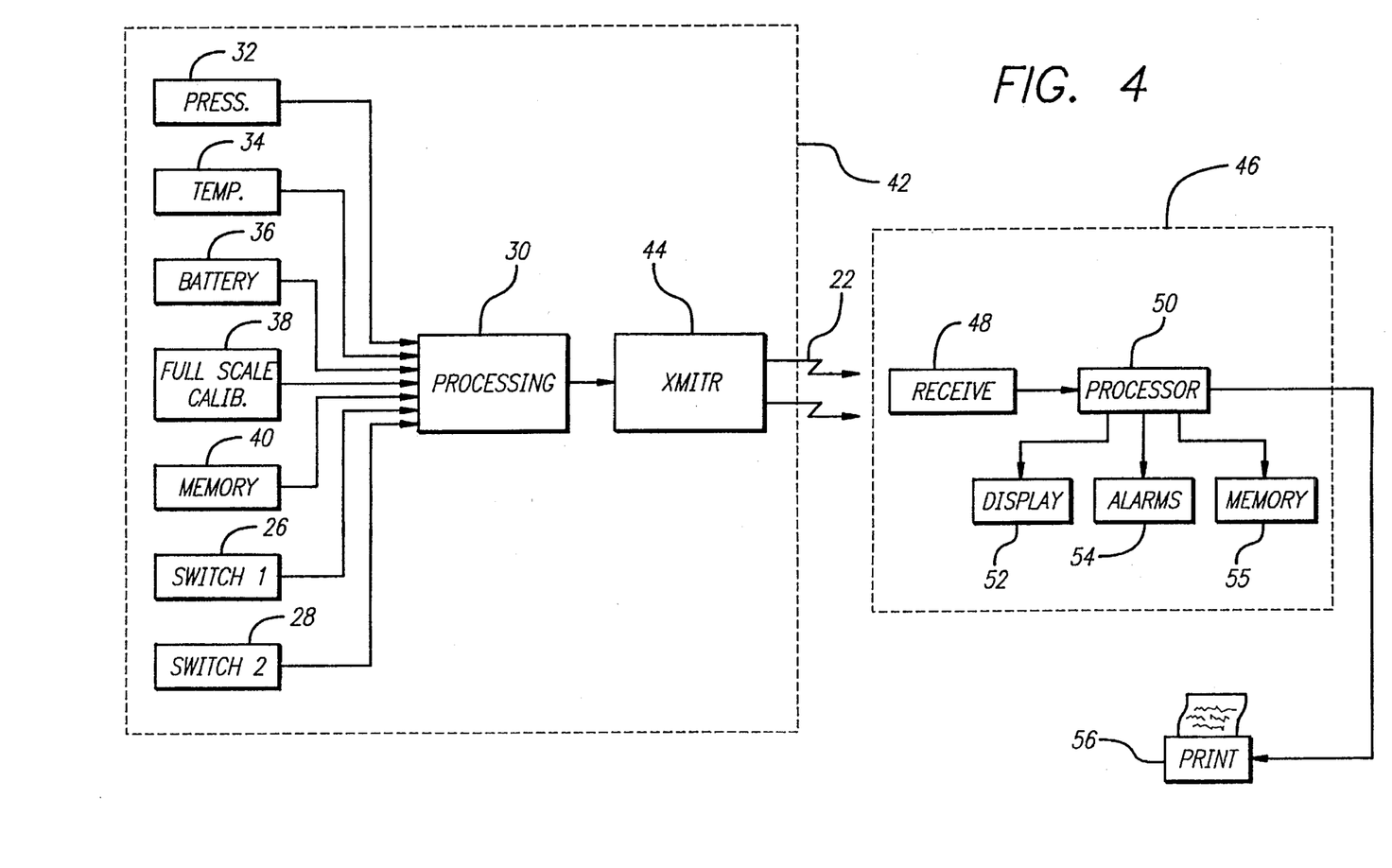
FIG. 4 is a block diagram of one embodiment of a communication system in accordance with the invention.

Referring now to FIG. 4, a block diagram of an embodiment of a communication system 10 in accordance with aspects of the invention is shown. In this embodiment, numerous sensor inputs are provided to processing circuitry 30 located at the portable medical device. The processing circuitry 30 may include a discretely implemented multiplexer and encoder. In this embodiment, a pressure sensor 32, a temperature sensor 34, and a battery voltage sensor 36 are all coupled to the processor 30. The status of control switches 26 and 28 are also coupled to the processor 30. Also disposed at the portable medical device is a calibration device 38 and a memory 40. The calibration device 38 comprises values indicative of a characteristic or characteristics of the pressure sensor 32, such as offset, to be used in processing the sensor's output. This device 38 may take the form of an active device, such as a programmed EEPROM or a passive device or devices, such as a resistor or resistor bank. The portable medical device's memory 40 may contain manufacturing data about the sensor 32 such as the serial number and expected battery life of the sensor/transmitter portion 42 of the communication system 10. In the alternative, the memory 40 may contain both calibration data and manufacturing data.

In accordance with an aspect of the invention, the processor 30 of the portable medical device receives the sensor and control signals and processes them into a predetermined signal pattern. In one embodiment, this signal pattern is a multiplexed form that is applied to the transmitter 44. The transmitter processes this pattern and radiates a signal 22 containing the information.

The receiver portion 46 of the communication system 10 is located at the remote console 14. The receiver 48 receives the transmitted signal 22, derives the predetermined signal pattern from it, and derives the data and control signals from the signal pattern. These signals are provided to the receiver processor 50 for processing into appropriate signals for graphical display 52, alarms 54, storage in a memory 55 and/or recording 56 such as by the printer shown in the figure. The memory 55 may comprise a magnetic disk, optical medium or other medium.

The control switches 26 and 28 of the portable medical device may be used to remotely program the receiver portion 46 of the remote console of the communication system. Alarm thresholds may be set by programming certain factors. For example, the maximum pressure permitted, and the maximum duration of the inflation period for this catheter may be set by use of the control switches. Referring again to FIG. 1, the remote console may be programmed to alert the practitioner that a threshold has been exceeded both on screen 15, such as by a graphical alarm notice, and/or by an audio alarm.

One switch 26 on the portable medical device may be labeled "SELECT" and used to toggle through a list of possible choices in a screen 15 menu while the other switch 28 may be labeled "ENTER" and used to choose the option indicated. Their functions are familiar to those skilled in the art. As an alternative, the practitioner may program the remote console 14 manually through switches located on the remote console itself 14. As shown in FIGS. 1 and 2 dedicated or fixed switches 21 and 23 corresponding to the switches 26 and 28 on the portable medical device 12 may be used for front panel control. In the case shown in FIG. 3, "soft" or programmable switches have been provided. The right-most switch 61 has been programmed for the function of selecting the menu. Its programmed function "MENU" is presented on the display 15 immediately above the switch. In this case, the remaining three switches have no programmed functions at this time. While four switches are shown, this not to be interpreted as a limitation. More or fewer switches may be used depending on the application. Additionally, such switches may be located around the screen in other positions. For example, they may be mounted vertically along the sides of the screen.

Figure 5:
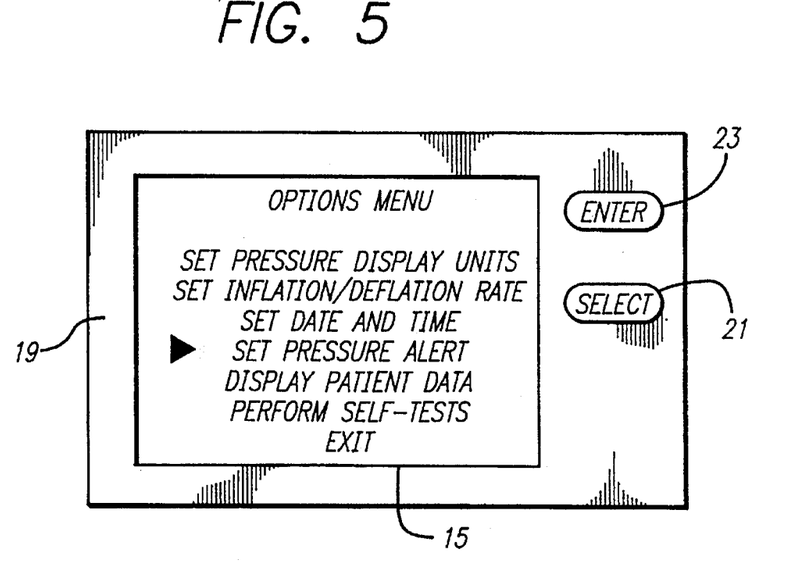
FIGS. 5 and 6 present sample menu displays showing the operation of a cursor in making menu selections.
Figure 6:
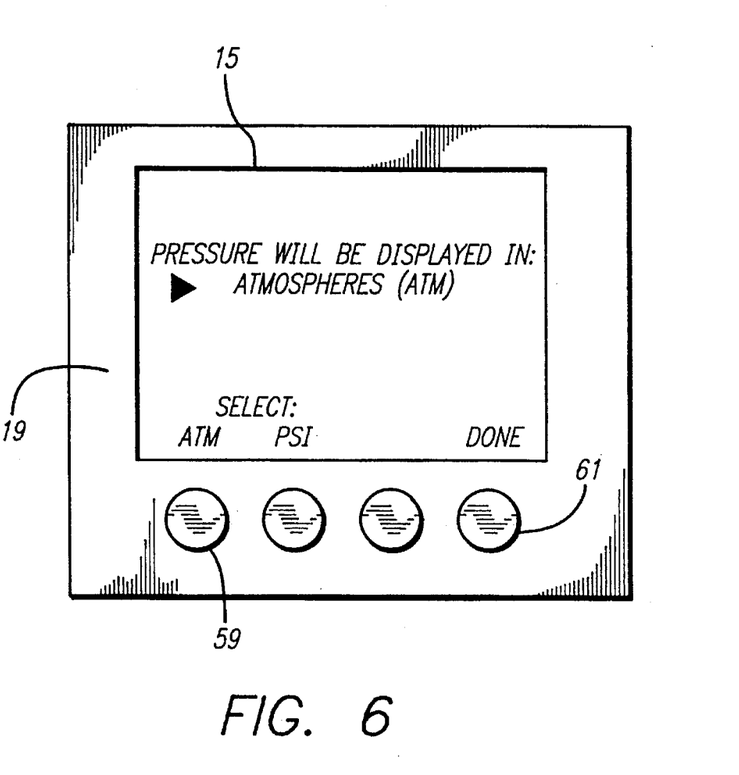

Referring now to FIGS. 5 and 6, sample front panel menus are shown. In FIG. 5, an options menu is shown and in FIG. 6, a sub-options menu for selecting the units of pressure is shown. In both cases, the arrowhead cursor may be scrolled up and down through the menu by pressing the "SELECT" switch 26 on the portable medical device 12 or the "SELECT" switch 21 on the front panel 19. The menu item to which the cursor points may be selected by pressing the "ENTER" switch 28 on the portable medical device 12 or the "ENTER" switch 23 on the front panel 19.

In FIG. 6, the soft keys have been assigned functions and in this case, scrolling on the screen is not necessary. For example, pressing soft key 59 has resulted in the choice of "atmospheres" as the display units. Another selection feature is shown in FIG. 2. The cursor in this embodiment moves horizontally along the bottom of the display. Currently it is at "GRAPH." Pressing "SELECT" will cause it to move horizontally. While FIGS. 2, 5 and 6 present different techniques for remote menu control, other techniques are possible.

Figure 7:
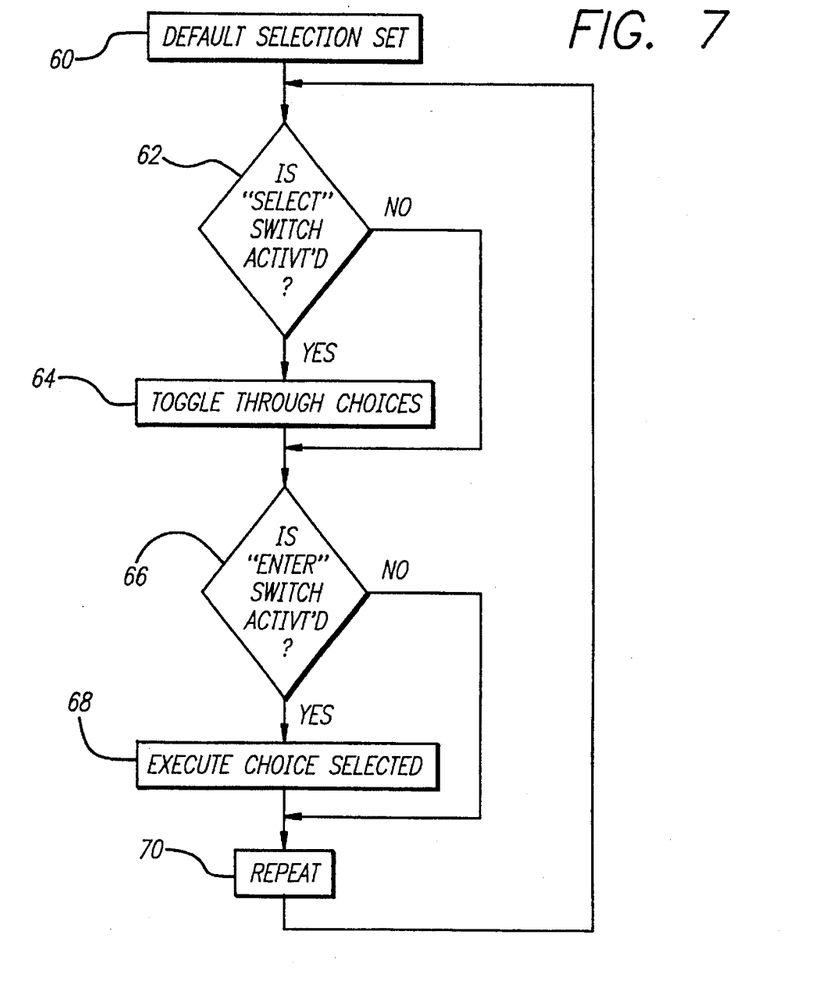
FIG. 7 presents a flow chart of a menu and selection program operating at the console, usable with the two switch embodiment of FIG. 1.

Referring now to FIG. 7, a flow chart of a programming process is presented. A default selection set is in place 60. Pressing the "SELECT" switch 26 on the portable medical device 12 would cause the processor 50 to engage a "menu" mode where a list of variables that may be altered is presented. A first menu may appear on the screen 15 of the remote console 14 having certain choices. Examples are shown in FIGS. 5 and 6.

In this decision block 62, the operator may sequence through the displayed list by pressing the "SELECT" switch 26 on the portable medical device 12. Each time the "SELECT" switch is pressed, the cursor moves to the next item per block 64. At the desired entry, the operator would press 66 the "ENTER" switch 28. An arrowhead as shown in FIGS. 5 and 6 or other cursor or indicating means, such as reverse video on a menu bar, would be used to assist in the selection of items. The remote console processor 50 would then move to another menu of selections or leave the set mode if the exit selection were chosen 68. Through this technique, only two control switches are needed at the portable medical device to achieve a wide range of control. The loop 70 is continuously repeated because the console is always polling for a switch closure.

After the variables for the portable medical device are set, the communication system 10 may be set to an operational status and the signals from the pressure sensor and other sensors associated with the medical device 12 received by the remote console 14. The remote console may begin monitoring these signals and graphically displaying data.

Figure 8:
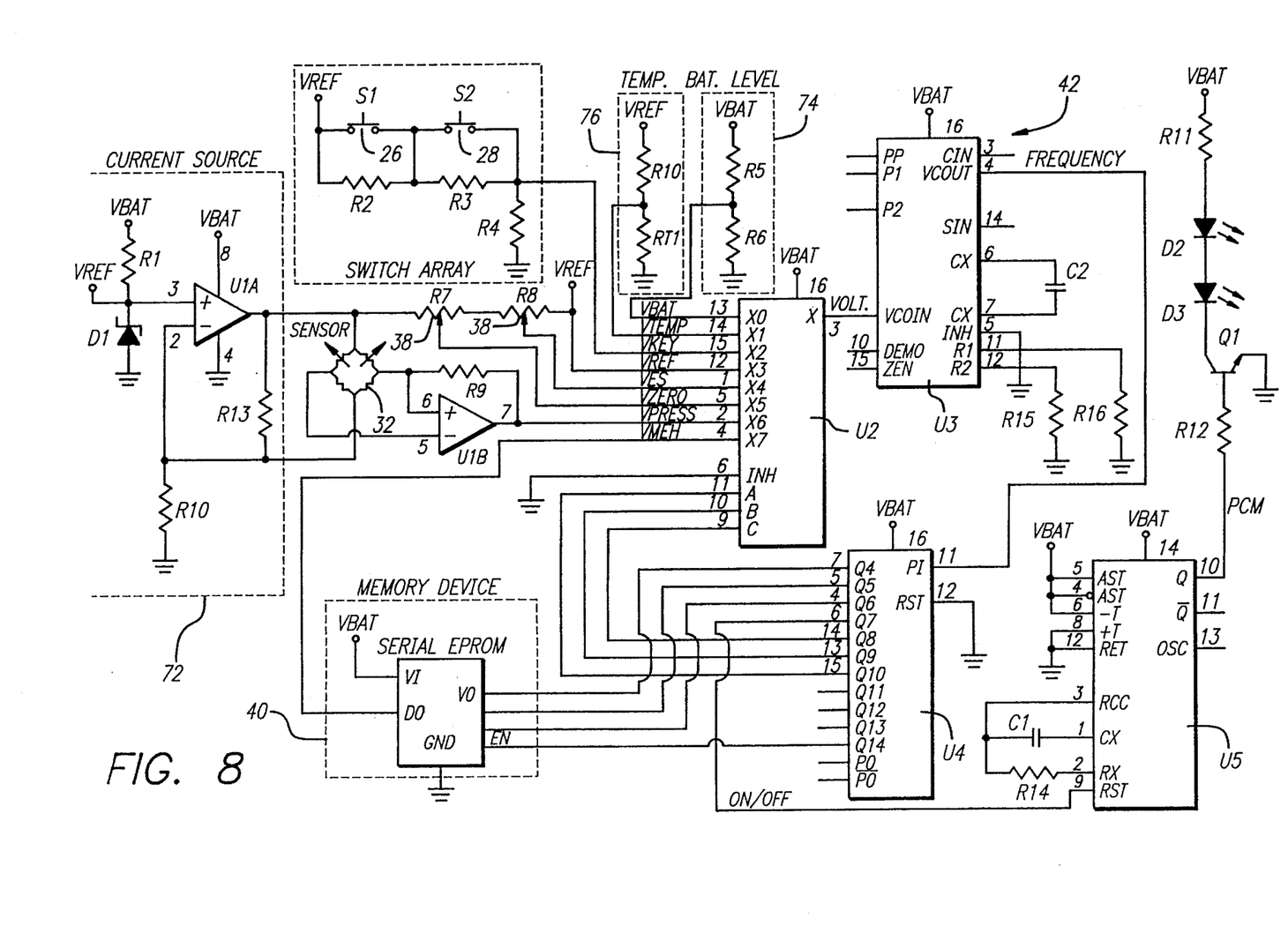
FIG. 8 presents a circuit diagram of a non-microprocessor control circuit in the medical device including a pressure sensor unit, a signal conditioning and encoding unit and a transmitter unit implemented with discrete components.

Referring now to FIG. 8, a schematic diagram of the transmitter section 42 of an embodiment of the communication system in accordance with the invention is shown. This embodiment has no microprocessor but instead relies discrete element digital logic for all functions. A battery is provided that has a certain voltage $V_{bat}$ as shown at the left side of the figure. A constant current source 72 is formed for powering the pressure sensor 32. The zener diode D1 functions to create a constant voltage independent of the varying battery voltage. Amplifier U1A develops an output voltage sufficient to cause the voltage across R10 to be equal to the zener diode voltage. Because the resistance of R10 is constant, the result is that the current through R10 is constant and independent of battery voltage. Because this current is constant, the current through the pressure sensor 32 and its compensating resistor R13 is constant, which minimizes the temperature coefficient of the pressure sensor.

The analog output of the pressure sensor 32 as well as an analog voltage encoding the status the two control switches S1 and S2 are provided to an analog multiplexer circuit U2. A battery sensor circuit 74 senses the battery voltage and provides the battery voltage signal to the multiplexer U2. A temperature sensor circuit 76 senses the temperature of the balloon dilatation fluid, and provides the temperature signal to the multiplexer. Additionally, potentiometers R7 and R8 supply voltages to the multiplexer indicative of characteristics of the pressure sensor for calibration purposes. In this embodiment, the voltage from R8 indicates the full scale of the sensor and the voltage from R7 indicates the offset or zero correction.

The output of the multiplexer U2 is input to the voltage controlled oscillator (VCO) circuit U3. The center frequency of the VCO is determined by C2 and R16. The VCO frequency increases with increasing input voltage with the minimum frequency at a zero voltage input determined by R15.

The VCO output frequency is the clock input to a fourteen stage binary counter U4. The outputs from stages Q8, Q9 and Q10 are provided to control the multiplexer channel selection. The counter selects the next channel after counting up to 256. After counting up to 256 on channel seven, the counter will select channel zero, etcetera. Counter output Q7 is provided to enable (active high) oscillator U5. The oscillator frequency (IR carrier) is determined by C1 and R14. The output of U5 has a 50% duty cycle and controls transistor Q1 that sinks current through the IR LEDs D2 and D3 at the carrier frequency. The carrier frequency in this embodiment is set to 40 kHz. Q7 output is high for a count of 128 or one-half the count of Q8. Using Q7 to gate Q1 instead of Q8 allows for a 25% duty cycle that conserves battery power and provides a convenient demarcation between channels. In the above manner the portable medical device data and control signals are multiplexed, modulated and transmitted to the remote console for display. It will be noted that the information is carried by the length of the burst of the 40 kHz pulses. This technique may be referred to as a pulse duration modulation scheme for transmitting information.

One advantage of this embodiment is that it permits a relatively inexpensive implementation because no microprocessor is involved. However, should the price of microprocessors decrease, they may be incorporated rather than the discrete element approach shown and described herein. In addition, the remote console can readily discern the presence of more than one portable medical device transmission because the duty cycle will appear greater than 25%. Upon detecting a received duty cycle of greater than 25%, the remote console can alert the practitioner to ensure only a single transmission is being received.

Figure 9:
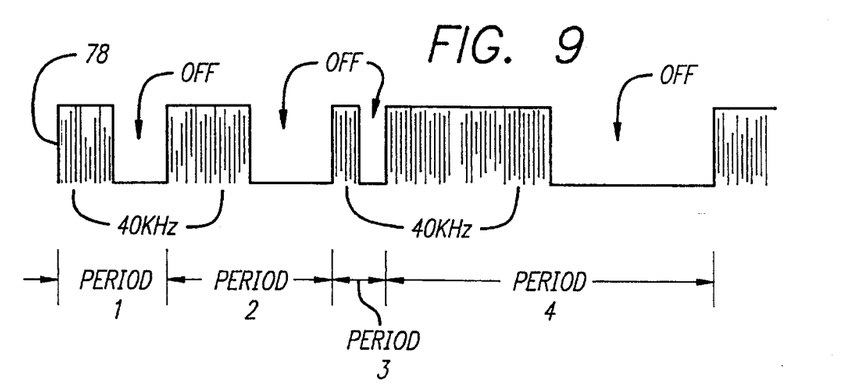
FIG. 9 presents a sample waveform showing a sample duty cycle useful in detecting the presence of more than one IR transmission.

FIG. 9 presents a diagram of a sample waveform 78 showing that for each period, one-half of it is in the form of a burst square-wave while the other one-half is off. This approach results in easier detection of more than one transmitter being on at the same time. In this embodiment, the output is narrowband AM at 40 kHz for a narrow band low noise receiver. The data frame shown provides serial voltage measurements that can include measured values, switch settings, battery status, and even values from a PROM to provide factory calibration information. With this approach, the data rate can support ten measurements per second. Additionally, a low battery condition can be detected before the data becomes inaccurate.

Referring again to FIG. 8, the output of the oscillator U5 is applied to two infrared light emitting diodes D2 and D3 by controlling the base of the transistor Q1. The LED's are disposed in series on the collector of the transistor Q1. In this embodiment, the LED's are oriented at an angle to each other, such as ninety degrees, so that wider angular acceptance results, providing more reliable communication.

Figure 10:
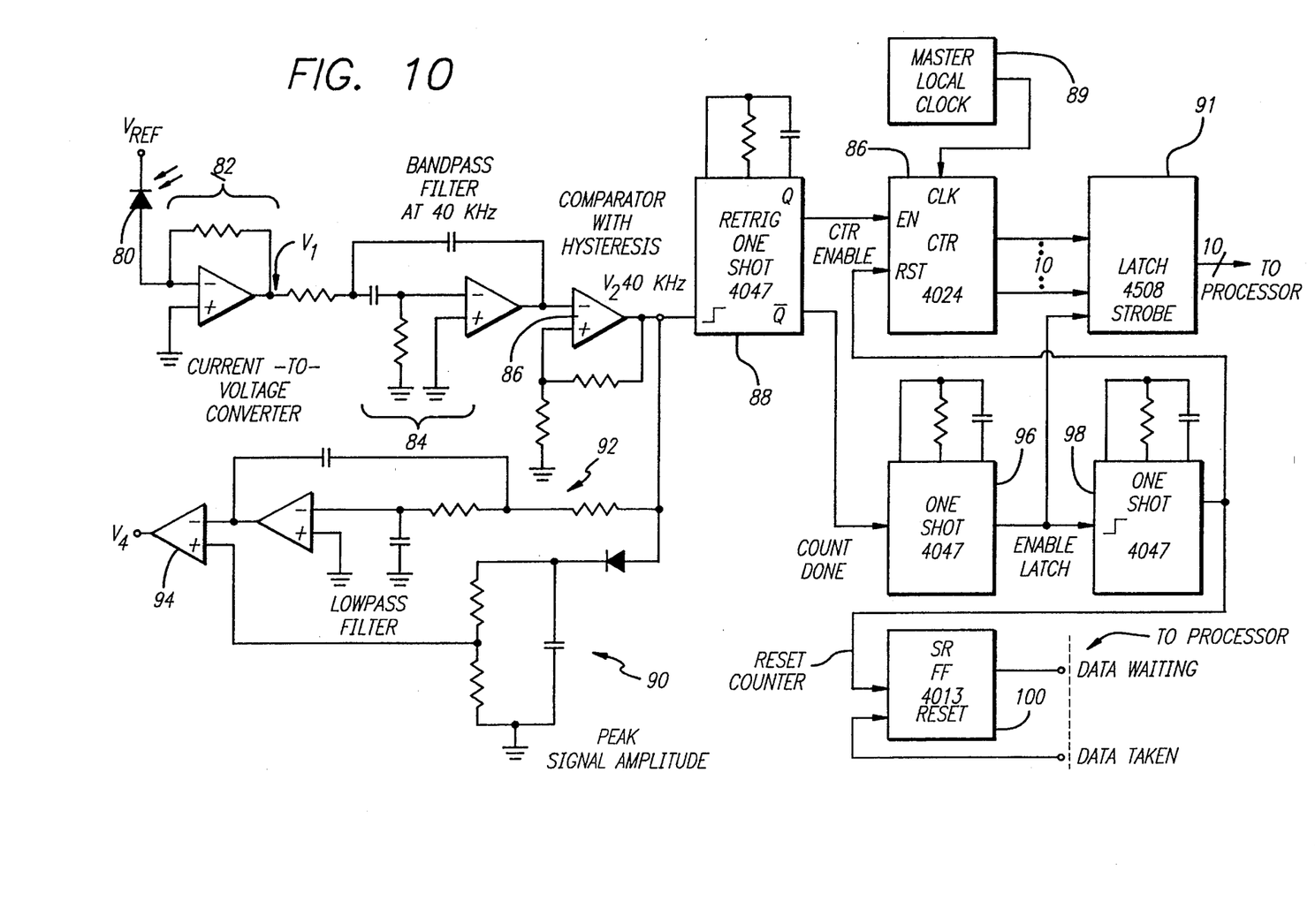
FIG. 10 presents a circuit diagram of a non-microprocessor receiver unit also implemented with discrete elements and including a detection circuit for the presence of more than one IR transmission.

Referring now to FIG. 10, a receiver is shown. The receiver circuit comprises an IR detector diode 80 that receives the IR pulse duration modulation signal from the portable medical device. The detector 80 generates a current proportional to the light intensity of the signal, which is a duplicate of the on/off waveform generated by U5 (see FIG. 8) that contains the data and control information.

The signal from the detector 80 is converted 82 to a voltage, bandpass filtered 84 and processed through a comparator 86 with hysteresis to result in a "clean" AM 40 kHz signal at V₂. The signal is processed through a retriggerable one-shot device 88 and clocked by the local master clock 89 through a counter 86 to determine the number of 40 kHz pulses present in a data interval. That number is stored in a latch 91 for use by the processor 50 (see FIG. 2).

The processor reads the latch 91 and processes the individual sensor and control signals for graphical display 52. The master local clock is counted while the 40 kHz signal is on. Another one-shot device 96 receives the "count done" signal from the retriggerable one shot 88. In response, this one shot 96 issues an "enable latch" signal to the latch device 91 and another one shot 98 is used as a time delay. The latter one shot 98 then provides a "reset counter" signal to a SetReset flip flop 100 ("SR FF") and to the counter 86. The SR FF is used as an interface to the processor and provides a "Data Waiting" signal. Upon receipt of this signal, the processor may read the count from the latch 91. The processor then provides a "Data Taken" signal to the SR FF 100 that resets the SR FF 100. Because of this reset, the SR FF will not again indicate to the processor that data is waiting until the latch 91 again reads a new count from the counter 86.

Thus, it can be appreciated that this modulation technique employs a scheme whereby the number of 40 kHz pulses contains the information transmitted. The number of 40 kHz pulses varies in dependence upon the voltage signals sensed. The receiver counts the number of 40 kHz pulses to determine the information sent.

Figure 11A:
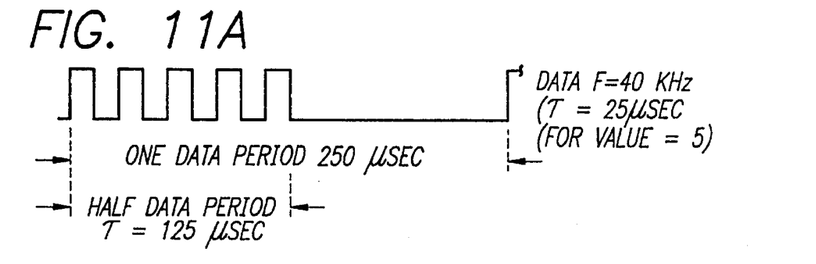
FIGS. 11A through 11F provide timing diagrams of a portion of the circuitry of FIG. 10.
Figure 11B:
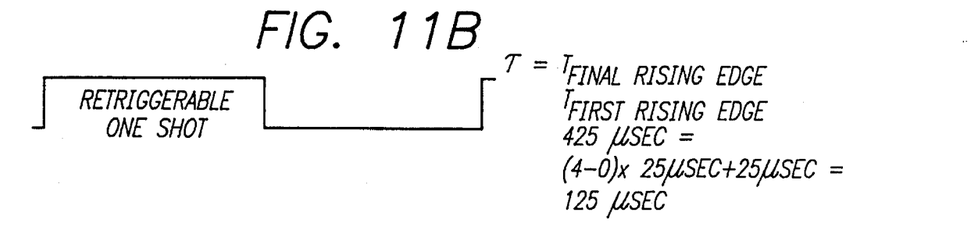
Figure 11C:
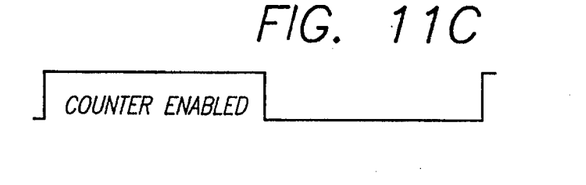
Figure 11D:
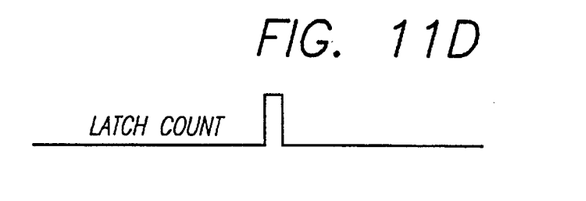
Figure 11E:
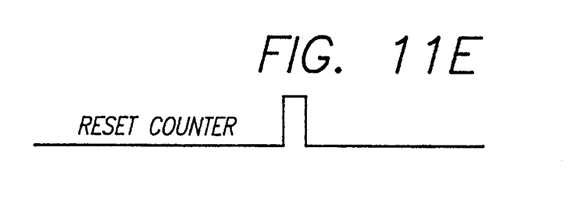
Figure 11F:
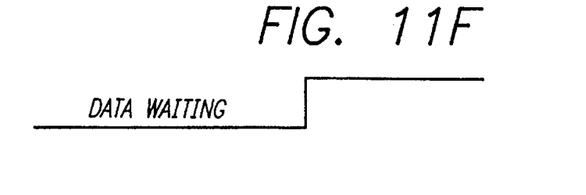

Timing diagrams of the above-described operation are furnished in FIGS. 11A through 11F. In FIG. 11A, data is provided for one-half period. The retriggerable one shot 88 receives that data throughout the period as shown in FIG. 11B. Additionally, in FIG. 11C, the counter 86 is enabled and proceeds to count. The latch 91 is strobed and receives the count in FIG. 11D. In FIG. 11E, the counter 86 is reset and in FIG. 11F, the "Data Waiting" signal is provided to the processor by the SR FF 100.

In accordance with this circuitry, a demultiplexer per se is not required by the processor 50. The "frame" of data is marked in the transmitter by two zero channels and the processor reads the received signal in accordance with the latched value and the preprogrammed position in the frame of the different signals. As the processor 50 receives sequential values, each will correspond to one position of the multiplexer. Because two of the channels are zero, they serve as the frame sync, allowing the identity of each channel to be determined.

Also shown in FIG. 10 is circuitry to detect the presence of more than one IR transmission. The duty cycle of the received signal is monitored. If the duty cycle is too high, it is presumed that more than one IR transmission has occurred simultaneously and an alarm is given to the operator. If the duty cycle detected is equal to the duty cycle of a single transmitter; i.e., 25%, only a single transmission if presumed and no alarm is given.

In FIG. 10, the voltage V₂ is also provided to a peak detector circuit 90 and a low pass filter 92 in parallel. Both output signals from these two circuits are compared 94 and if the output of the comparator is high, multiple IR transmissions exist and an alarm is given. If the signal is low, only one IR transmission is detected and no alarm would be given.

In the embodiment shown above, the following parts were used:

| Part No. | Model No. | Manufacturer |
|---|---|---|
| U1A/U1B | ICL7621 | RCA |
| U2 | 4051 | RCA |
| U3 | 4046 | RCA |
| U4 | 4060 | RCA |
| U5 | 4047 | RCA |
| D1 | LM385-1.25 | National Semiconductor |
| D2/D3 | | Hewlett Packard |
| Q1 | 2N2222 | Motorola |

Additional values and designation numbers for the elements shown in FIG. 8 are as follows:

| | |
|---|---|
| C1 | 1000 P |
| C2 | .01 µF |
| R1 | 4.7K |
| R2 | 10K |
| R3 | 4.7K |
| R4 | 4.7K |
| R5 | 10K |
| R6 | 10K |
| R7 | 10K |
| R8 | 10K |
| R9 | 4.7K |
| R10 | 10K |
| R10 | 220 |
| R11 | 47 |
| R12 | 150 |
| R13 | TCOMP |
| R14 | 4.7K |
| R15 | 4.7K |
| R16 | 22K |
| RT 1 | T°- |

Although pressure is the principal physiological parameter sensed and measured in the preferred embodiment, other parameters such as temperature and battery voltage may be sensed and measured. Furthermore, although a manually controlled inflation device is shown in the embodiment above, the invention may be applied to other types of inflation systems. For example, a motor driven system may include a communication system in accordance with the invention. One or more switches may be added to the portable medical device to control the motor as required.

While specific embodiments of the invention have been described in detail, it will be appreciated by those skilled in the art that various modifications to the structure and use of the disclosed invention may be made in light of the overall teachings of the disclosure, without departing from the scope of the invention as defined by the appended claims.

We claim:

1. A system for communicating data from a portable medical device to a remote console and displaying that data at the remote console, the medical device including a first sensor disposed to sense a physiological parameter and provide data signals representative of the sensed parameter, the remote console including a monitor for displaying the data provided by the portable medical device, the system comprising:

a control switch disposed at the portable medical device that provides a control signal for controlling a selected operation of the remote console;

a first circuit disposed at the portable medical device and coupled to the first sensor, the first circuit processing the control signal and the data signals representing the sensed physiological parameter into a predetermined signal pattern;

a transmitter disposed at the portable medical device for receiving the predetermined signal pattern from the first circuit and radiating energy in accordance with the signal pattern;

a battery disposed at the portable medical device for providing power to the first circuit and the transmitter;

a receiver disposed at the remote console for receiving the radiated energy and predetermined signal pattern from the transmitter and deriving the data signals and the control signal from the received energy;

a processor disposed at the remote console that processes the derived data signals from the receiver and provides graphic display signals representing the derived data signals; and wherein the monitor disposed at the remote console displays the graphic display signals received from the processor on a screen in graphic format.

2. The system of claim 1 further comprising:

a battery sensor disposed at the portable medical device that senses a battery parameter indicative of the remaining battery life and provides a battery level signal representative thereof;

wherein the first circuit is coupled to the battery sensor and receives the battery level signal and processes it into the predetermined signal pattern.

3. The system of claim 1 further comprising:

a temperature sensor disposed at the portable medical device that senses a temperature at the medical device, the temperature sensor providing a temperature signal representative of that sensed temperature;

wherein the first circuit is coupled to the temperature sensor and receives the temperature signal and processes it into the predetermined signal pattern.

4. The system of claim 1 wherein the first circuit comprises a multiplexer that receives the data signals from the first sensor and multiplexes them into a multiplexed signal;

wherein the predetermined signal pattern comprises the multiplexed signal.

5. The system of claim 1 wherein the receiver further comprises:

interference means for monitoring received energy to determine if the received energy has been provided by more than one transmitter;

wherein the monitoring means provides an interference alarm signal in the event that more than one transmitter is detected.

6. The system of claim 1 wherein the first circuit comprises a non-microprocessor control circuit consisting of discrete elements.

7. The system of claim 1 wherein the console further comprises:

an historical memory device that stores and catalogs the data received from the portable medical device for later recall;

wherein the processor is coupled to the historical memory and is adapted to store the derived data in the historical memory;

wherein the processor is also adapted to retrieve the stored data from the historical memory.

8. The system of claim 1 wherein the processor disables the control of certain console functions by the control signal when the sensed parameter has a quantity other than a predetermined quantity.

9. The system of claim 1 further comprising:

a characteristic memory device disposed at the portable medical device that provides data related to calibration of the portable medical device;

wherein the first circuit in the portable medical device incorporates the calibration data from the memory device into the predetermined signal pattern;

wherein the receiver in the remote console derives the calibration data from the received energy;

wherein the processor in the remote console processes the calibration data.

10. The system of claim 1 further comprising:

a characteristic memory device disposed at the portable medical device that provides data related to battery life of the portable medical device;

wherein the first circuit in the portable medical device incorporates the battery life data from the memory device into the predetermined signal pattern;

wherein the receiver in the remote console derives the battery life data from the received energy;

wherein the processor in the remote console processes the battery life data.

11. A system for monitoring and displaying data on a console representative of the pressure in a dilatation balloon system for use in a medical procedure, in which a pressure sensor provides data signals representative of the sensed balloon pressure, the system comprising:

a control switch mounted at the balloon system that provides a control signal;

a first circuit disposed at the balloon system and coupled to the pressure sensor and the control switch, the first circuit processing the data signals representing the sensed pressure and the control signal into a predetermined signal pattern;

a receiver disposed at the console for receiving the predetermined signal pattern and deriving the data signals and control signal from the pattern;

a processor disposed at the console that processes the derived data signals from the receiver and provides graphic display signals representing the derived data signals and other display signals pertinent to the medical procedure; and a display disposed at the console that displays the graphic display signals received from the processor on a screen in graphic format.

12. The system of claim 11 wherein the processor provides display signals comprising numbers, alphabetical characters, and graphical designs with which information is presented in a graphic format on the display concerning the medical procedure.

13. The system of claim 11 wherein the console further comprises a switch located adjacent the display; wherein the processor indicates on the display screen the function of the switch when activated.

14. The system of claim 11 wherein the console further comprises:

a historical memory device that stores and catalogs the data received from the balloon system for later recall;

wherein the processor is coupled to the historical memory and is adapted to store the derived data in the historical memory;

wherein the processor is also adapted to retrieve the stored data from the historical memory.

15. The system of claim 14 wherein the processor is adapted to display the retrieved data in a predetermined graphical format on the display screen.

16. The system of claim 14 wherein the processor is adapted to output the retrieved data from the console in a form usable by a printer.

17. The system of claim 11 wherein:

the processor disables the control of certain console functions by the control switch when the pressure sensed is above a predetermined value.

18. The system of claim 11 wherein the transmitter comprises:

a modulation circuit based on a steady carrier frequency that is coupled to the predetermined signal pattern to form pulses;

wherein an infrared light emitting device is coupled to the modulation circuit for receiving the pulses;

wherein the light emitting device generates infrared energy in accordance with the modulation circuit.

19. A method for communicating data from a portable medical device to a remote console, the medical device including a first sensor disposed to sense a physiological parameter and provide data signals representative of the sensed physiological parameter, the remote console including a monitor for displaying the data provided by the portable medical device, the method comprising the steps of:

receiving the data signals representing the sensed physiological parameter from the first sensor and processing the received signals into a predetermined signal pattern at the portable medical device;

providing a control signal from the portable medical device for controlling selected operations of the remote console;

processing the control signal into the predetermined signal pattern;

modulating a transmitter signal at the portable medical device in accordance with the predetermined signal pattern and radiating the transmitter signal;

providing power from a battery located at the portable medical device for generating the predetermined signal pattern and the radiated energy;

receiving the radiated energy at the remote console and deriving the data signals and control signal from the received energy;

processing the received data signals and control signal at the remote console and providing graphic display signals representing the derived data signals; and displaying the graphical display signals at the remote console on a screen in graphic format.

20. The method of claim 19 further comprising the steps of:

sensing a battery parameter indicative of the remaining battery life and providing a battery level signal representative thereof;

processing the battery level signal into the predetermined signal pattern.

21. The method of claim 19 further comprising the steps of:

sensing a temperature at the portable medical device and providing a temperature signal representative of that sensed temperature; and processing the temperature signal into the predetermined signal pattern.

22. The method of claim 19 further comprising the step of:

multiplexing the sensor data into a multiplexed signal;

wherein the predetermined signal pattern comprises the multiplexed signal.

23. The method of claim 19 further comprising the steps of:

monitoring received energy to determine if the received energy has been provided by more than one transmitter;

providing an interference alarm signal in the event that more than one transmitter is detected.

24. The method of claim 19 further comprising the steps of:

storing the data received from the portable medical device for later recall in an historical memory disposed at the remote console; and retrieving the stored data from the historical memory.

25. The method of claim 19 further comprising the steps of disabling the control of certain console functions by the control signal when the sensed parameter has a quantity other than a predetermined quantity.

26. The method of claim 19 further comprising the steps of:

storing at the portable medical device data related to a characteristic of the portable medical device;

incorporating the characteristic data from the memory device into the predetermined signal pattern;

deriving the characteristic data from the received energy;

processing the characteristic data at the remote console.

27. The method of claim 26 wherein the step of storing characteristic data includes the step of storing manufacturing data about the portable medical device.

28. A communication system for communicating data and a control signal between a portable device and a remote console, the portable device including a first sensor disposed to sense a parameter and provide data signals representative of the sensed parameter, the portable device having a control switch providing the control signal when activated, the remote console including a monitor for displaying the data provided by the portable device, the system comprising:

a battery disposed at the portable device for providing power to the portable device;

a battery sensor disposed at the portable device that senses a battery parameter indicative of the remaining battery life and provides a battery level signal representative thereof;

a non-microprocessor control circuit comprising discrete elements disposed at the portable device and coupled to the first sensor, the battery sensor, and receiving the control signal, the control circuit multiplexing said signals into a predetermined signal pattern; and a transmitter disposed at the portable device for receiving the predetermined signal pattern from the control circuit and radiating energy in accordance with the signal pattern.

29. The communication system of claim 28 wherein the transmitter transmits the predetermined signal pattern in infrared energy.

* * * * *